(12) United States Patent
Evertsz (10) Patent No.: US 7,366,676 B2
(45) Date of Patent: Apr. 29, 2008

(54) METHOD AND SYSTEM FOR IN-SERVICE MONITORING AND TRAINING FOR A RADIOLOGIC WORKSTATION

(75) Inventor: Carl J. G. Evertsz, Bremen (DE)

(73) Assignee: MeVis Breastcare GmbH & Co. KG, Breman (DE)

(*) Notice: Subject to any disclaimer, the term of this patent is extended or adjusted under 35 U.S.C. 154(b) by 1243 days.

(21) Appl. No.: 09/870,388

(22) Filed: May 29, 2001

(65) Prior Publication Data
US 2002/0194019 A1 Dec. 19, 2002

(51) Int. Cl.
*G06Q 50/00* (2006.01)
(52) U.S. Cl. ............... 705/2; 705/3; 434/262; 600/408
(58) Field of Classification Search ............. 705/2–3; 434/262; 600/408
See application file for complete search history.

(56) References Cited

U.S. PATENT DOCUMENTS

| | | | | |
|---|---|---|---|---|
| 4,411,628 A | * | 10/1983 | Laughon et al. ............ | 434/169 |
| 4,807,110 A | | 2/1989 | Pomerene et al. | |
| 5,061,187 A | * | 10/1991 | Jerath ......................... | 434/262 |
| 5,306,154 A | * | 4/1994 | Ujita et al. ................. | 434/218 |
| 5,560,360 A | * | 10/1996 | Filler et al. ................ | 600/408 |
| 5,819,288 A | * | 10/1998 | De Bonet .................... | 707/2 |
| 5,890,911 A | * | 4/1999 | Griswold et al. ............ | 434/322 |
| 5,917,929 A | | 6/1999 | Marshall et al. | |
| 5,987,345 A | | 11/1999 | Engelmann et al. | |
| 6,011,862 A | * | 1/2000 | Doi et al. .................... | 382/132 |
| 6,021,404 A | * | 2/2000 | Moukheibir ................. | 706/46 |
| 6,041,135 A | | 3/2000 | Buytaert et al. | |
| 6,058,322 A | * | 5/2000 | Nishikawa et al. .......... | 600/408 |
| 6,084,594 A | * | 7/2000 | Goto ........................... | 345/427 |
| 6,098,064 A | | 8/2000 | Pirolli et al. | |
| 6,127,669 A | | 10/2000 | Sidiropoulos et al. | |
| 6,128,002 A | * | 10/2000 | Leiper ......................... | 345/156 |
| 6,151,662 A | | 11/2000 | Christie et al. | |
| 6,154,767 A | | 11/2000 | Altschuler et al. | |
| 6,154,826 A | | 11/2000 | Wulf et al. | |
| 6,260,021 B1 | * | 7/2001 | Wong et al. .................. | 705/2 |
| 6,283,761 B1 | * | 9/2001 | Joao ............................. | 434/236 |
| 6,535,714 B2 | * | 3/2003 | Melker et al. ............... | 434/350 |
| 6,540,679 B2 | * | 4/2003 | Slayton et al. ............... | 600/439 |
| 6,551,107 B1 | * | 4/2003 | Buckley et al. .............. | 434/262 |
| 6,669,482 B1 | * | 12/2003 | Shile ........................... | 434/262 |
| 2002/0076091 A1 | * | 6/2002 | Wang ........................... | 382/132 |

OTHER PUBLICATIONS

Anonymous. "Ampersand Medical Announces Samba Telemedicine Imaging Contract With French Regional Government" Nov. 2000. vol. 19, Iss. 7, p. 22.*

* cited by examiner

*Primary Examiner*—C. Luke Gilligan
*Assistant Examiner*—Mike Tomaszewski
(74) *Attorney, Agent, or Firm*—Martin Fleit; Paul D. Bianco; Fleit Kain Gibbons Gutman Bongini & Bianco P.L.

(57) ABSTRACT

In a method and a computer system for screening of medical cases known proven positive and/or known proven normal cases are inserted in the flow of cases during the screening. On a user's option the known cases can be infiltrated in the case stream in accordance with a fixed pattern or on a random basis. When the radiologist makes a misdiagnosis of a known case this is recognized by the system and a corresponding output message is provided to the radiologist. Further the system has a database for tracing all user actions, including the diagnostic findings for the purposes of generating a user action report, quality control and assurance, and support in litigation.

11 Claims, 9 Drawing Sheets

Fig.1

| User ID | Case ID | Diagnosis | Diagnosis Correct ? | User Actions | Time spent on case |
|---|---|---|---|---|---|
| | | | | | |
| | | | | | |
| | | | | | |
| | | | | | |
| | | | | | |
| | | | | | |
| | | | | | |

```
Total number of cases:      10 20 30 40 50 60 70 80 90 100    [30]  ⟵25
Number of suspicious cases:  ?                                      ⟵26
              min. number:   0 1 2 5 10 20 30                 [5]
              max. number:   0 1 2 5 10 20 30                 [5]   ⟵27

Choice and order of cases:   random/fixed

Start training
```

Fig.5

```
                             10 20 30 40 50 60 70 80 90 100   [30]  ⟵25
Number of suspicious cases:  ?                                      ⟵26
              min. number:   0 1 2 5 10 20 30                 [5]
              max. number:   0 1 2 5 10 20 30                 [10]  ⟵27

Choice and order of cases:   random

Start training
```

Fig.6

```
           Result Table
        (Case Selected Correct)

01        +
         02        +
         03        -      -
         04        -      -
         05        -      -
         06        -      -
         07        +
         08        -      -
         09        -      -
         10        +

Correctly:   6 (60%)
Incorrectly: 4 (40%)
False pos.:  0
False neg.:  4
Time: 0 min 47 s Show solutions
New training set
```

| cases | results | | elapsed time |
|---|---|---|---|
| Case018 | | ★ | 5 s |
| Case023 | Not correctly judged | ★ | 4 s |
| Case033 | Not correctly judged | ★ | 6 s |
| Case044 | | | 8 s |
| Case088 | Not correctly judged | ★ | 8 s |
| Case092 | | | 6 s |
| Case441 | | | 8 s |

Ok

METHOD AND SYSTEM FOR IN-SERVICE MONITORING AND TRAINING FOR A RADIOLOGIC WORKSTATION

CROSS REFERENCES TO RELATED APPLICATIONS

This application is related to the following patent applications, filed at the same day as this application and assigned to the same assignee, MeVis Technology GmbH & Co. KG
(1) A method and computer system for prefetching of images, Ser. No. 09/870,389; filed May 29, 2001;
(2) A method and computer system for screening of medical cases, Ser. No. 09/870,386; filed May 29, 2001;

which are hereby incorporated by reference to be understood in connection with the present invention.

FIELD OF THE INVENTION

The invention relates a method and apparatus for use in the field of screening of medical cases, and more particularly to training, quality control and quality assurance for the screening of medical cases. Further, the invention relates to a method and system for in-service monitoring and training for a radiologic workstation.

BACKGROUND AND PRIOR ART

In a radiologic screening procedure, such as screening mammography, true abnormalities such as cancers are believed to occur at a typical rate of about three to four cases per one thousand patient examinations. Apparently any misdiagnosis of the radiologist can have drastic consequences for the patient. However when a large number of cases is screened it is unavoidable that the radiologist's attention decreases over time.

U.S. Pat. No. 5,917,929 shows a user interface for a computer aided diagnosis (CAD) system. The CAD system serves as an electronic reminder or second reader to assist radiologists in obtaining higher detection rates or higher sensitivity for abnormalities. In addition the CAD system assists radiologists in reducing the misdiagnosis rate, or lowering the false negative rate. However, the usage of a CAD system and a user-friendly interface does not address the problem of lapse of the attention of the radiologist, which decreases due to fatigue or other reasons.

U.S. Pat. No. 5,987,345 discloses a method and system for displaying of medical images. The system displays an image along with corresponding ones of the same image with computer-aided diagnostic information added. The CAD computer output is used as a second opinion prior to the final decisions of the radiologist. Again the problem of a decreasing attention of the radiologist is not addressed here.

SUMMARY OF THE INVENTION

It is an object of the present invention to provide a novel method, apparatus and system for screening of medical images.

It is another object of the present invention to provide for improved training, quality assurance and quality control for the screening of medical images.

It is a further object of the present invention to provide a quality report for the screening procedure performed by a radiologist, which can be relied upon by regulatory authorities, health insurance providers, and/or legal authorities in case of litigations.

These and other objects of the invention are achieved by a method, apparatus and system which infiltrates known proven positive and/or known normal cases, in the sequence of cases to be reviewed, in a fixed or random manner. In brief, the infiltration of known positive cases serves to monitor and control the radiologist's attention. This mode of operation is also referred to as "in-service monitoring" or "radiologist's performance monitoring".

Another application of the present invention is for the purposes of training. For this application, the radiologist does not review actual cases; rather the radiologist reviews known cases having a certain user definable absolute number, statistical frequency and/or distribution of a variety of medical case categories.

The very low incidence rate of 3 to 4 per 1000, make screening mammography particularly demanding on radiologist's concentration. The infiltration of known positive cases is a way to artificially increase the incidence rate of cancers in screening.

In a preferred embodiment the absolute number or percentage of known cases to be infiltrated is specified by the super user. Further, the categories of known cases to be infiltrated can also be selected, as well as, the statistical distribution of various categories of the known cases to be infiltrated.

The invention is advantageous in that it provides an immediate feedback to the radiologist during the screening procedure so that the radiologist can recognize a decreasing level of concentration and/or fatigue. For example when one or more misdiagnosis of known cases occurs, the user can be asked by the system to take a break. Alternatively, the system can be disabled for the respective radiologist for a certain predetermined time period for appropriate recovery of the radiologist.

All user actions (e.g. keyboard, mouse clicks and system tools used) concerning the real cases to be reviewed, as well as, the known cases and the diagnosis and feedback provided to the user can be traced. Based on the tracing, a user action report can be generated for the purposes of quality monitoring and control. Such a report can even be relied upon for the defence against claims for damages due to a misdiagnosis.

BRIEF DESCRIPTION OF THE DRAWINGS

A more complete appreciation of the invention and many of the attendant advantages thereof will be readily understood from the following detailed description of preferred embodiments when considered in connection with the accompanying drawings, wherein.

DESCRIPTION OF THE PREFERRED EMBODIMENTS

Figure 1:
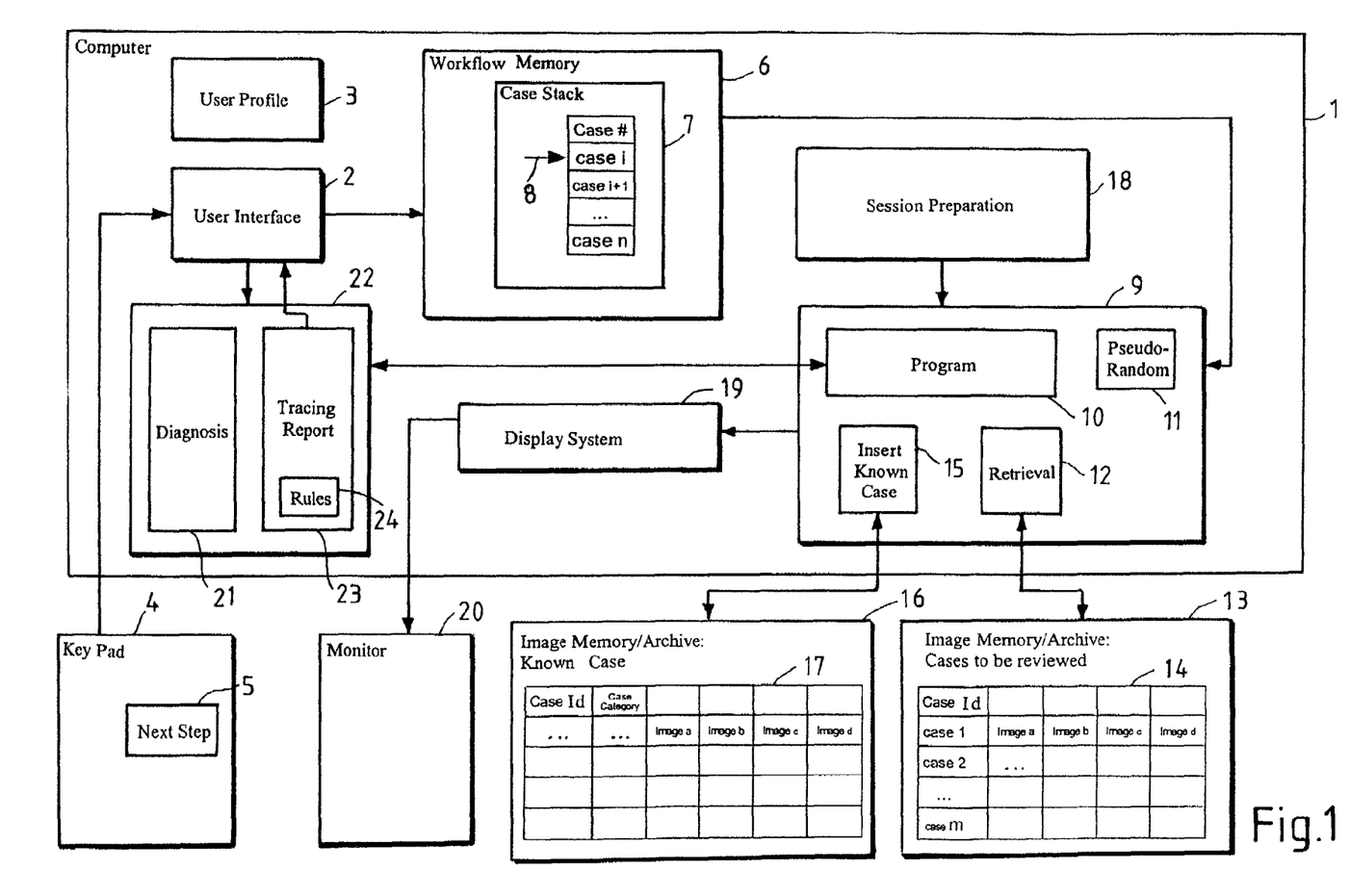
FIG. 1 is a diagram of the system according to the invention.

Referring now to the drawings, in particular FIG. 1, a preferred embodiment of the invention will be described.

FIG. 1 shows a diagram of the computer system according to the invention. The computer system has a computer 1 with a user interface 2. For each user of the computer 1, a user profile 3 can be stored. A keypad 4 is connected to the user interface 2. The keypad 4 has a next-step button 5. If a user presses the next-step button 5, this is a direction to the user interface 2 such that the computer 1 is caused to go to the next image or case.

The user interface 2 is coupled to workflow memory 6, which stores a workflow for the screening procedure. The workflow memory 6 contains a case stack 7 for storage of the case numbers to be reviewed in a particular screening procedure to be performed by a particular user. In the example considered here, the case stack 7 contains the cases with ID numbers ranging from i to n. The case stack 7 has a pointer 8 for pointing to the current case that is being reviewed by the user of the computer 1. At the time considered here, the pointer 8 points to the case i, which is the first case of the case stack 7.

The workflow memory 6 is coupled to the image selection module 9 that contains a program 10 and a pseudo-random number generator 11. Further the image selection module 9 contains a retrieval program module 12 for coupling to a database 13 and for retrieval of image data from the database 13. The database 13 can be implemented on a mass storage of the computer 1 or on an external server computer, such as an external image archive, as is the case in the example of FIG. 1.

The database 13 contains a table 14 of cases and the corresponding image data for each of the cases. In the example considered here, the table 14 contains the cases from case 1 to case m, each of the cases having respective images a, b, c, d.

For screening mammography, typically four (or eight) images are taken per case: a left and a right craniocaudal image and a left and a right mediolateral oblique image (and the priors from the previous screening round). Each of the cases contained in the table 14 of the database 13 can be accessed by means of the respective case identifier (ID) that serves as a key for performing the database query.

The image selection module 9 further comprises an infiltration program module 15 that is coupled to a database 16. Again, the database 16 can be stored on a mass storage of the computer 1, such as a CD-ROM, or it can be stored on a separate server computer.

The database 16 has a table 17 for storage of known proven positive and/or known proven normal cases. Each of the known cases of the table 17 has a unique case ID that serves to retrieve a particular case from the table 17. Each of the cases has a data record containing the image data for the case as well as data indicating the category of the case. Again, in the case of screening mammography, each case can have four images a, b, c, d, corresponding to a left and a right craniocaudal and a left and a right mediolateral oblique view, or eight images if the priors from the previous round are used also.

The case category can contain four different data fields corresponding to the category of the tumour, the breast density, the mammographic findings (lesion type) and a subtlety rating. The table below gives an example of a classification scheme for the case category. Each sub-category of a case is identified by a specific value as indicated in the table below.

TABLE I

| Case Category | Name of case category | Value for case category |
|---|---|---|
| 1 | Category of tumor | 00 = normal (no tumor) |
|   |   | 11 = benign tumor |
|   |   | 22 = cancer screen detected |
|   |   | 33 = interval cancer (over-looked, false negative) |
|   |   | 44 = interval cancer (true) |
| 2 | Breast density | 1 = <5% |
|   |   | 2 = 5-25% |
|   |   | 3 = 25-50% |
|   |   | 4 = 50-75% |
|   |   | 5 = >75% |
| 3 | mammographic findings (lesion type) | mass |
|   |   | calcification |
|   |   | architectural distortion |
|   |   | asymmetry |
|   |   | other (specify. . .) |
|   |   | (l) left, (r) right, link to annotations |
| 4 | subtlety rating | 1. extremely subtle |
|   |   | 2. very subtle |
|   |   | 3. subtle |
|   |   | 4. relatively obvious |
|   |   | 5. obvious |

The infiltration program module 15 can query the database 16 in order to identify the known cases in the table 17 having a required category or corresponding to a certain profile of sub-categories in accordance with the above table I. In the latter case the required case category or sub-category serves as a key to identify suitable cases for the infiltration.

The image selection module 9 is coupled to the session preparation module 18. The session preparation module 18 allows specifying the cases to be screened in order to initialize the case stack 7. Further the session preparation module 18 allows inputting an absolute number or percentage of known cases to be inserted into the flow of cases being screened by the user. Further the session preparation module 18 enables specifying the absolute number or percentage of known cases of different categories and/or different category profiles in accordance with the above table I. The session preparation module 18 can serve both to initialize a real screening session as well as a training session with training cases.

The image selection module has an output connected to the display system 19, which serves to display a current image on the monitor 20. After having reviewed the current image, which is displayed on the monitor 20, the radiologist can input a diagnosis and/or an annotation via the user interface 2. The diagnosis and/or annotation is stored in the diagnosis database 21 of the database module 22.

The database module 22 further contains a user action database 23 for the tracing of user actions that are input via the user interface 2. The user action database 23 also serves for the purposes of generating the user action report in accordance with rules 24.

It is important to note that the computer system of FIG. 1 can be used both for training purposes and for the screening of real cases. In the case of training the user can initialize the operation of the computer system by means of the session preparation module. For example the user can select the number of known cases for the training session as well as the statistical distribution of known positive cases.

For the purposes of in-service radiologist's performance monitoring of a real screening session the session preparation by means of the session preparation module 18 is typically done by a super user and not by the radiologist who actually performs the screening operation. Typically the super user can initialize the computer system for a variety of different users, which are identified by respective user IDs.

For a particular user the case stack 7 is initialized to contain the cases to be reviewed by that user as well as a certain profile of known cases to be inserted into the flow of images. When the user considered here logs on, the corresponding case stack 7 and the other entries made by means of the session preparation module 18 by the super user are retrieved by means of the user profile 3.

When the user starts the screening procedure the program 10 obtains a pseudo-random number from the pseudo-random number generator 11 in order to decide whether the real case i to which the pointer 8 points is to be displayed or if a known case is to be displayed. If a real case of the case stack 7 is to be displayed the database 13 is queried in order to retrieve the case and to display the case.

If a known case is to be inserted into the flow of cases the program 10 performs an access operation to the database 16 via the infiltration program module 15 in order to retrieve an appropriate known case for display. It is not transparent to the radiologist whether a case that is currently displayed on the monitor 20 is a real case or a known case.

In both instances a diagnosis of the radiologist is entered via the user interface 2 and stored in the diagnosis database 21. In the case of a known case the diagnosis is compared to the ground truth and/or pathology. If a mismatch between the diagnosis and the ground truth and/or pathology occurs, this is recognized by the program 10, and a corresponding message is displayed on the monitor 20. For example the message can be "you missed a cancer" or similar.

The fact that a misdiagnosis occurred is stored in the user action database 23 as well as all other user actions. After the user has entered his or her diagnosis for the current case he or she can go to the next case by pressing the next-step button 5 such that the pointer 8 is shifted to the consecutive case but only if the last case has not been a known case. Again the program 10 makes a determination whether to display the consecutive case as identified by the pointer 8 or to display a known case from the database 16.

This procedure continues until all cases of the case stack 7 have been processed. If the number of misdiagnosis recognized by the program 10 gets above a certain predefined threshold level the program 10 can display a corresponding message to the radiologist and/or it can disable the operation of the computer 1 for a certain predefined period of time in order to allow an appropriate recovery of the radiologist. At the end of the screening or training session a report can be generated based on the contents of the user action database 23 in accordance with the rules 24. For example the user action report generation can utilize the following in-service monitoring indicators of tables II and III:

TABLE II

|  | malignant | non-malignant | |
|---|---|---|---|
| objectives (data) subjectives |  | Finding (lesion visible) | No finding (no lesion visible) |
| (diagnosis) | malignant | benign | Negative |
| Positive | A | B1 | B2 |
| Benign | C1 | D1 | D2 |
| Negative | C2 | D3 | D4 |

TABLE III

| Variable | Result | finding | malignant | Comment |
|---|---|---|---|---|
| A | true positive | YES-ok | YES-ok | Lesion found and correctly interpreted as malignant |
| B1 | False positive | YES-ok | YES-not ok | Classification error: a benign lesion is interpreted as malignant |
| B2 | False positive | YES-not ok | YES-not ok | something seen that is not there: something normal is interpreted as malignant |
| C1 | False negative | YES-ok | NO-not ok | Classification error: a malignant lesion is interpreted as benign |
| C2 | False negative | NO-not ok | NO-not ok | overseen: a malignant lesion is overseen |
| D1 | True negative | YES-ok | NO-ok | Lesion found and correctly interpreted as benign |
| D2 | True negative | YES-not ok | NO-ok | something seen that is not there, but classified as benign |
| D3 | True negative | NO-not ok | NO-ok | overseen: benign lesion not found, but the result is correct (benign) |
| D4 | True negative | NO-ok | NO-ok | no finding at all, result is correct |

Figure 2:
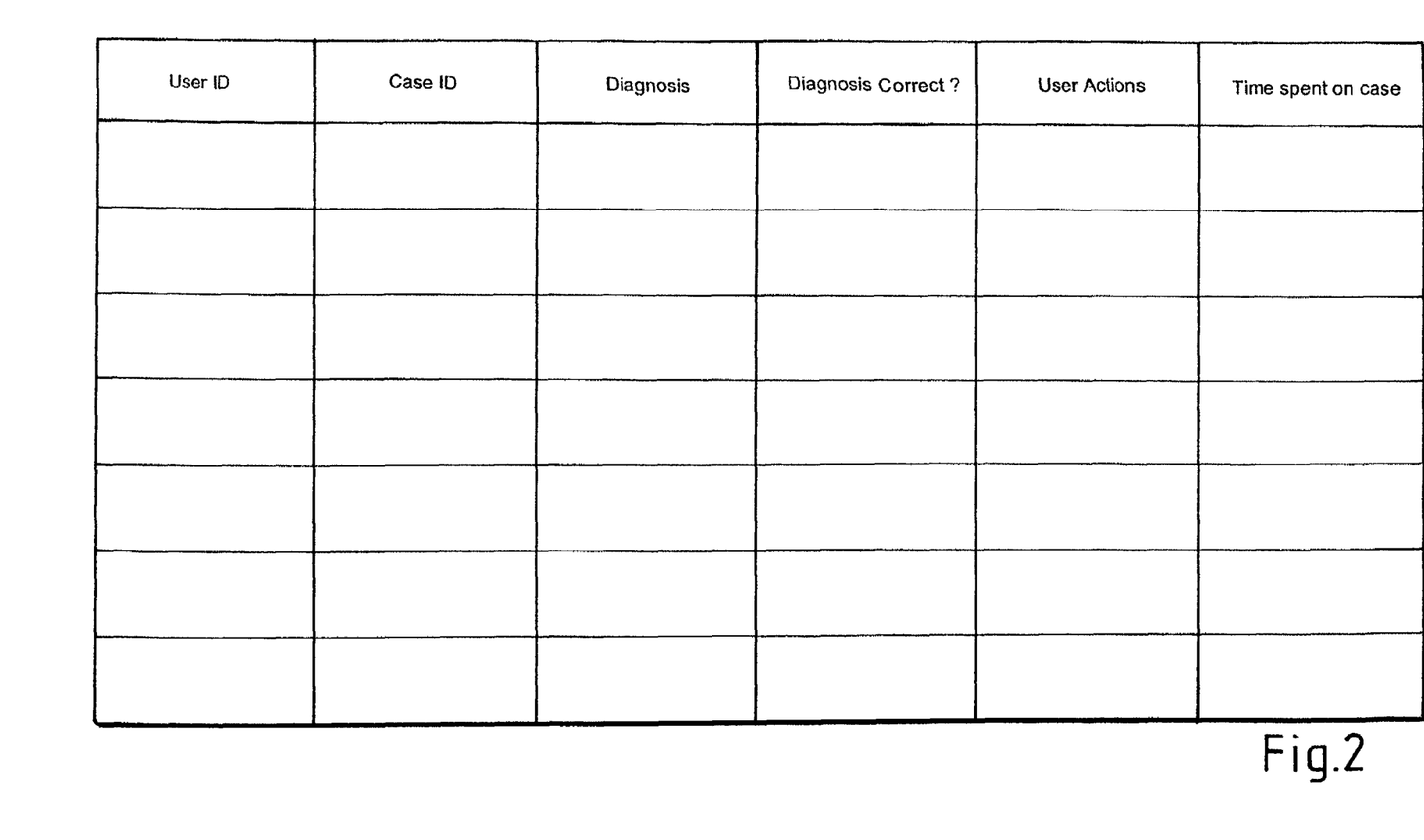
FIG. 2 is a diagram illustrating a database for the generation of a user action report.

FIG. 2 illustrates an example of the structure of the user action database 23. In the example of FIG. 2 the user action database 23 is structured as a table having the data fields "user ID", "case ID", "diagnosis", "diagnosis correct?", "user actions" and "time spend on case". The data field "user ID" contains the user ID of the radiologist who has reviewed a case that is identified by its case ID in the corresponding data field "case ID". The diagnostic findings of the radiologist, with the user ID, is indicated in the data field "diagnosis". Using the in-service monitoring indicators (A,B1, etc) the truth of this diagnosis can be determined and added in the "diagnosis correct?" column. For unknown screening cases, this column is empty.

The field "user actions" contains a trace of all user actions performed with respect to the case with the case ID. Examples for such user actions are the sequence of images requested by the radiologist for the review of the case, the format of the images requested, such as tiling of the monitor and magnification of the images, as well as image transformations and computer aided diagnosis functions which the radiologist uses for the review of the case. The following data field "time spent on case" contains the amount of time the radiologist has spent on the review of the particular case.

Figure 3:
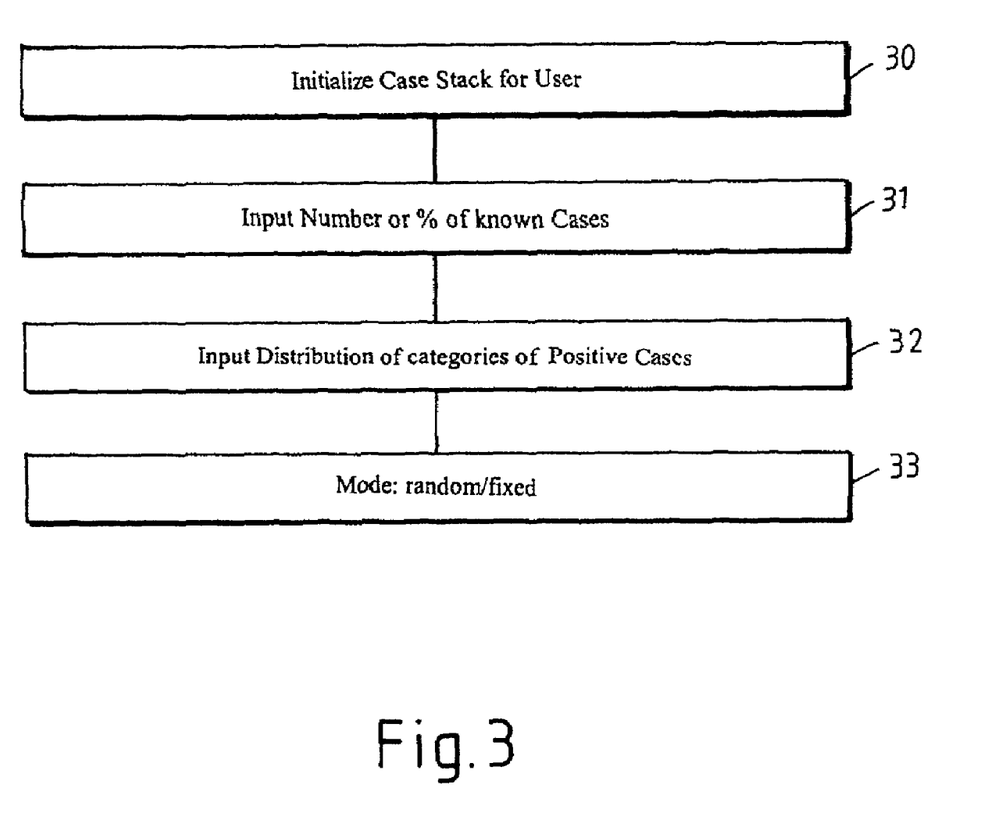
FIG. 3 is a flow chart illustrating the initialisation of the screening procedure.

FIG. 3 shows a flow chart for the initialization of the computer system of FIG. 1. In step 30, the case stack is initialized by specifying the cases to be reviewed by the user.

Typically, this is done by the super user in the case of a real screening procedure. For training purposes this can be done by the user himself.

In step 31 an absolute number or percentage of known cases to be infiltrated in the stream of cases is entered. Again this can be done by the super user or the radiologist himself, depending on the application.

Further in step 32 a distribution of the categories of the known cases can be entered such as by specifying a percentage value for each of the categories of above table 1. Further in step 33 the mode can be specified. If the random mode is selected the known cases are infiltrated randomly into the stream of cases. If the fixed mode is selected the known cases are infiltrated based on a fixed predefined pattern.

Figure 4:
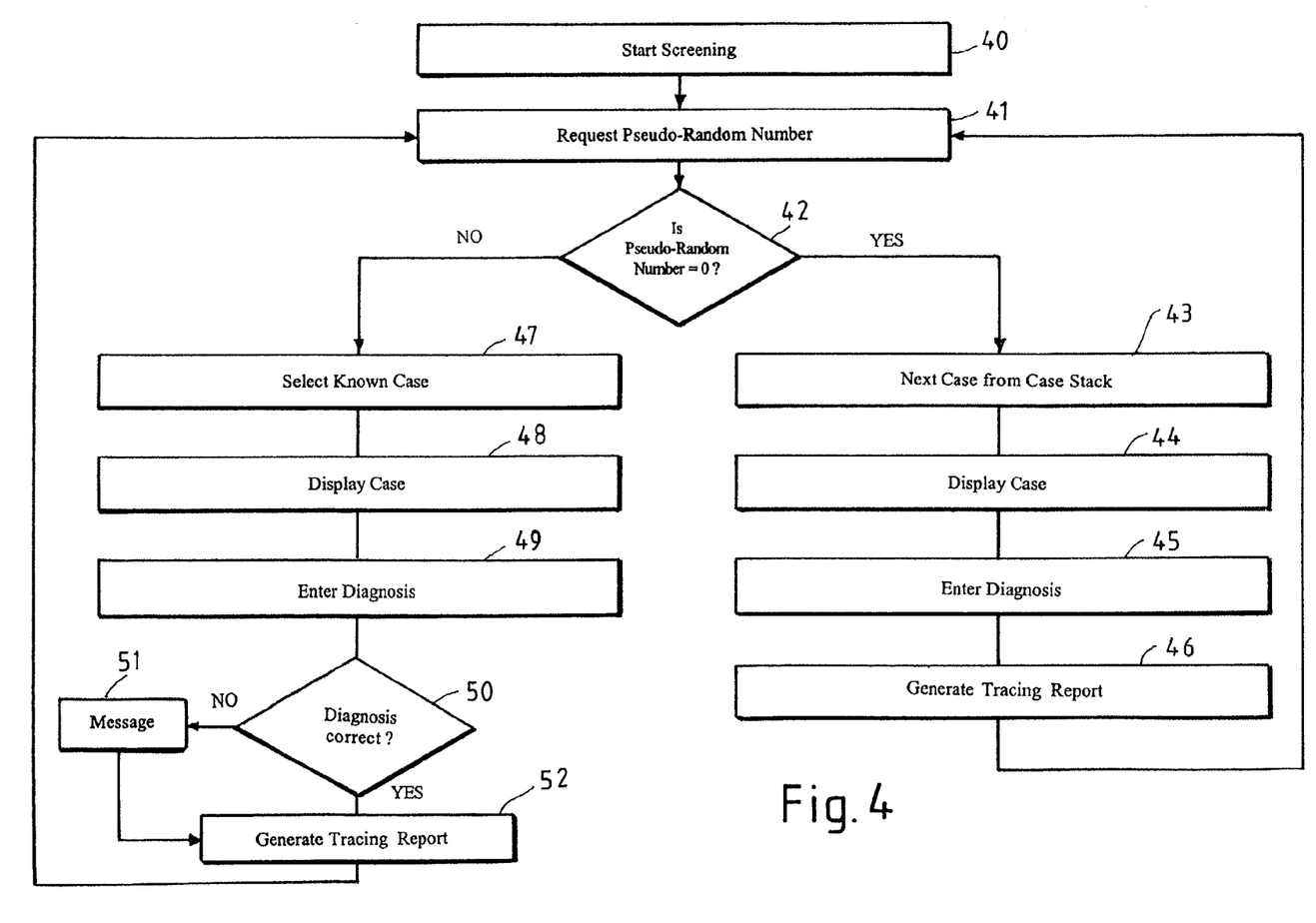
FIG. 4 is a flow chart illustrating an embodiment of the screening procedure in accordance with the invention.

In FIG. 4 the screening procedure is illustrated in greater detail. In step 40 the screening procedure is started by the radiologist. In order to display a first case for review by the radiologist a pseudo-random number is requested in step 41.

Based on the pseudo-random number a decision is made in step 42. If the pseudo-random number is equal to 0 this means that a real case from a case stack is to be displayed to the radiologist. A corresponding case from the case stack is identified in step 43 and displayed to the radiologist in step 44. In step 45 the radiologist can enter his or her diagnosis. Alternatively the radiologist can also decide not to enter the diagnosis. In this instance the actual case is shifted to the bottom of the case stack (cf. FIG. 1—case stack 7) for later review and diagnosis.

In step 46 the user action database 23 is updated for the storage of data corresponding to the data fields of the table of FIG. 2 with respect to the case that has been reviewed by the radiologist. After step 46 the control returns back to step 41.

In step 41 again a pseudo-random number is requested and it is again decided in step 42 whether the pseudo-random number equals 0. If the pseudo-random number is not equal to 0 the control goes to step 47 in order to select a known case.

The known case selected in step 47 is displayed in step 48 to the radiologist. After review of the case displayed in step 48 the radiologist enters the diagnosis in step 49. In step 50 it is decided whether the diagnosis entered in step 49 is correct or not.

If the radiologist classified the known e.g. positive case as a normal case (a verified case with no malignant abnormality) or as a negative case (a verified case with no abnormality, whether benign or malignant) the diagnosis for the known positive case is incorrect and the control goes to step 51 in order to output a corresponding message to the radiologist. For example a corresponding message can be displayed and/or an aural output such as a beep, can be outputted.

From step 51 the control goes to step 52 corresponding to step 46 in the case of a real medical case. If the diagnosis is correct the control goes directly from step 50 to step 52. From step 52 the control goes to step 41, such that the procedure is repeated again. This sequence of steps continues until all cases from the case stack have been processed in the screening procedure.

Figure 5:
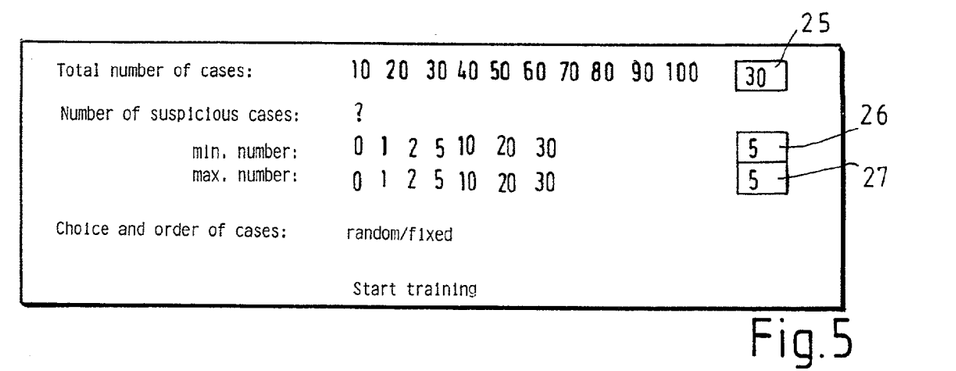
FIGS. 5 to 7 are illustrations of screens produced by the system according to the invention.
Figure 6:
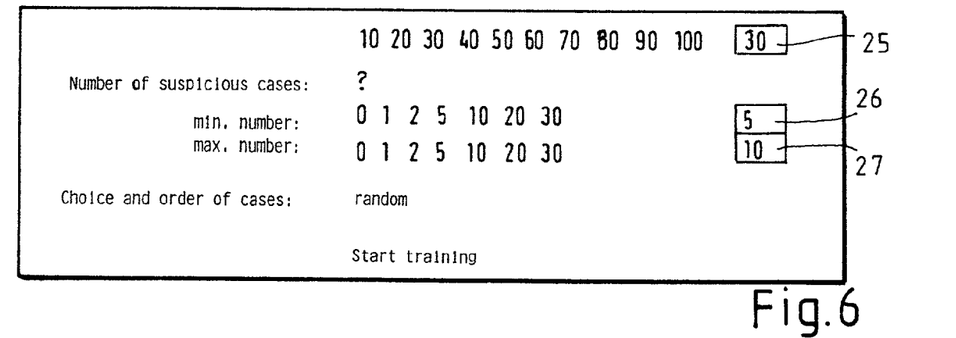
Figure 7:
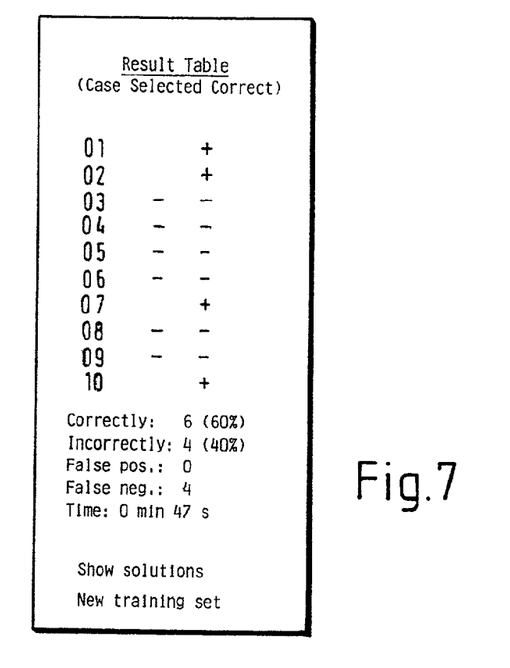

FIGS. 5 to 7 are illustrations of screens produced by the computer 1 of FIG. 1. FIG. 5 and FIG. 6 each show a screen of the training session preparation phase. In the screen of FIG. 5 the total number of cases to be reviewed can be entered in the input field 25. In the example considered here the user can chose between ten and one hundred cases. The user's choice is 30 cases in the example considered here. The chosen number of cases can be highlighted on the screen.

Further the user can specify the number of suspicious cases to be infiltrated in the case stream. The user can input a minimum number of suspicious cases in the input field 26 and the user can input a maximum number of suspicious cases in the input field 27. If only one of the input fields 26 and 27 is used or if the same number is input in both fields 26 and 27 the user can chose between the random and the fixed mode by clicking on the word "random" or "fixed". By clicking on "start training" the user can start the screening training procedure.

FIG. 6 shows the screen of FIG. 5 when the user has input different numbers in the input fields 26 and 27. In this case the only possible mode is the random mode of operation so that the user can directly click on "start training".

FIG. 7 shows an example of a report, which has been generated based on the user action database. The report was done for a screening session of ten cases 1 to 10. The result table of FIG. 7 shows the number of correct and incorrect diagnosis as well as the number of false positive and false negative cases. A false positive case is a case, which is classified by the radiologist as a positive case but which does not contain a malignant finding; a false negative case is a case which is classified by the radiologist as a negative case, but which does contain a malignant finding.

Further the average time spent for each individual case is indicated. On request a more detailed report can be generated based on the user action database.

By clicking on "show solutions" the system displays the correct diagnosis of the known positive cases. By clicking on "new training set" the control goes back to the screens of FIG. 5 and FIG. 6.

Figure 8:
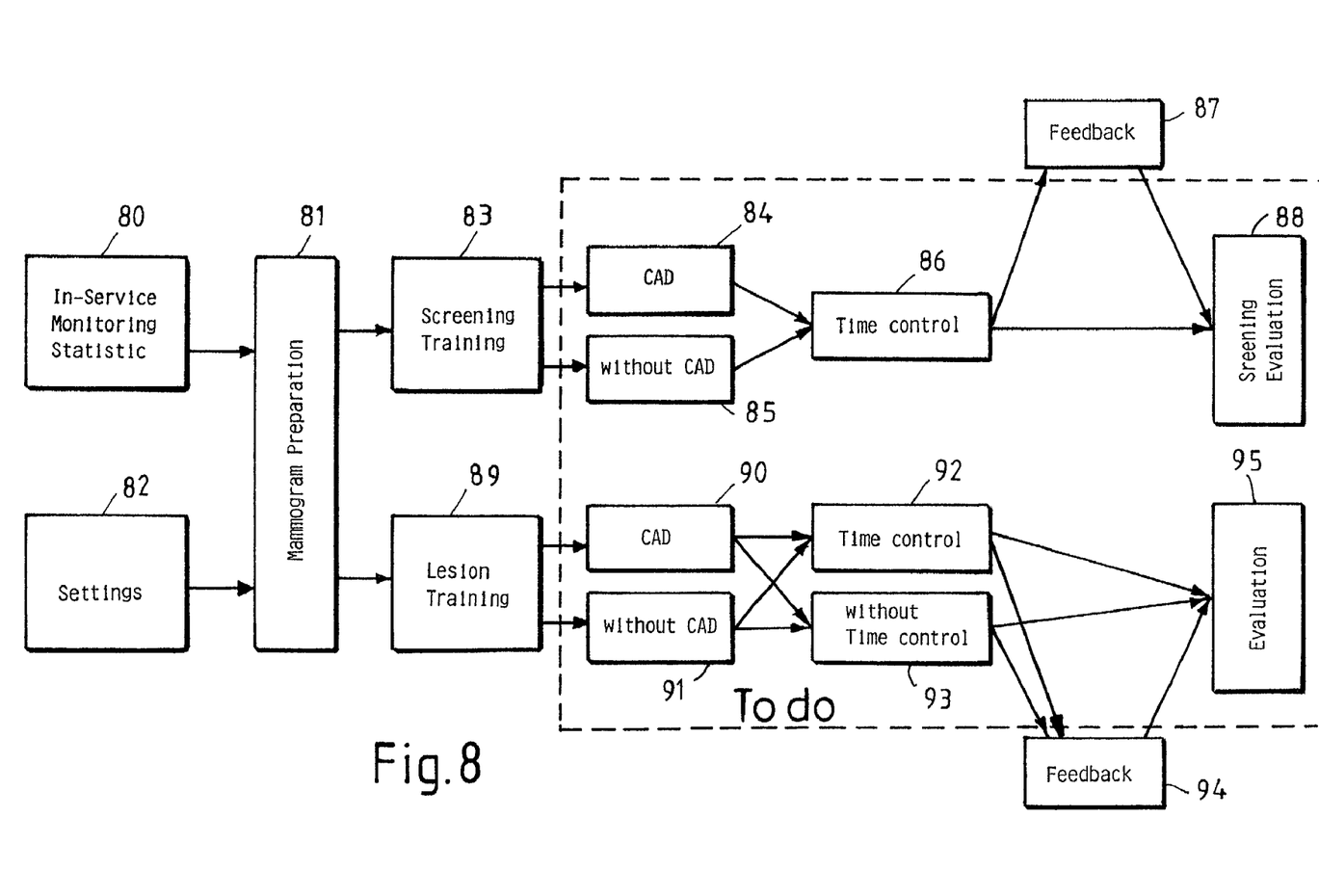
FIG. 8 is an alternative embodiment of the computer system of the invention allowing both screening training and lesion training.

FIG. 8 illustrates an alternative embodiment of the computer system and method of the invention allowing both screening training and lesion training. In step 80 of the flow chart of FIG. 8 an in-service monitoring statistic is provided. The in-service monitoring statistic can be provided by means of a user action report, which has been generated in accordance with step 52 of the flow chart of FIG. 4 (cf. user action data base 23 of FIG. 1).

The in-service monitoring statistic is indicative of the radiologist's performance. For example it contains the statistic of the success rate of the radiologist's diagnosis of the known cases. The statistic can be specific on the type of cases and can thus serve to identify case categories in which the radiologist's diagnoses are frequently incorrect.

The in-service monitoring statistic is a basis for the mammogram preparation (step 81). In step 81 a set of mammograms is selected depending on the in-service monitoring statistic provided in step 80. For example if the radiologist's performance is particularly weak for a certain case category known cases of this category can be selected and prepared for display.

Alternatively individual settings can be inputted in step 82. By means of the individual settings a specific case profile can be specified for selection and preparation in step 81. In step 83 a screening training is performed based on the mammograms prepared in step 81. The corresponding cases are displayed in steps 84 and 85 with and without computer aided diagnosis (CAD) software support, respectively. The time required for the radiologist for inputting his or her respective diagnosis is traced in step 86. As an option the radiologist gets immediate feedback in step 87, in particular in case of a wrong diagnosis.

The overall result of the screening is evaluated in step 88 and the evaluation is displayed to the user.

As an alternative to the steps 83 to 88 for the screening training a lesion training can be performed in step 89. In contrast to the screening training the lesion training cases only consist of known positive cases with a variety of different lesion categories to be correctly diagnosed by the user. Again the cases are displayed with and without CAD support in steps 90 and 91, respectively.

The time required for the diagnosis can be traced in step 92 at the user's option. Alternatively the inputting of the diagnosis can be performed in step 93 without time control. In either case the radiologist has the option to get immediate feedback in step 94, in particular in case of a misdiagnosis. In step 95 an overall evaluation of the performance of the radiologist for the lesion training is generated and displayed.

Figure 9:
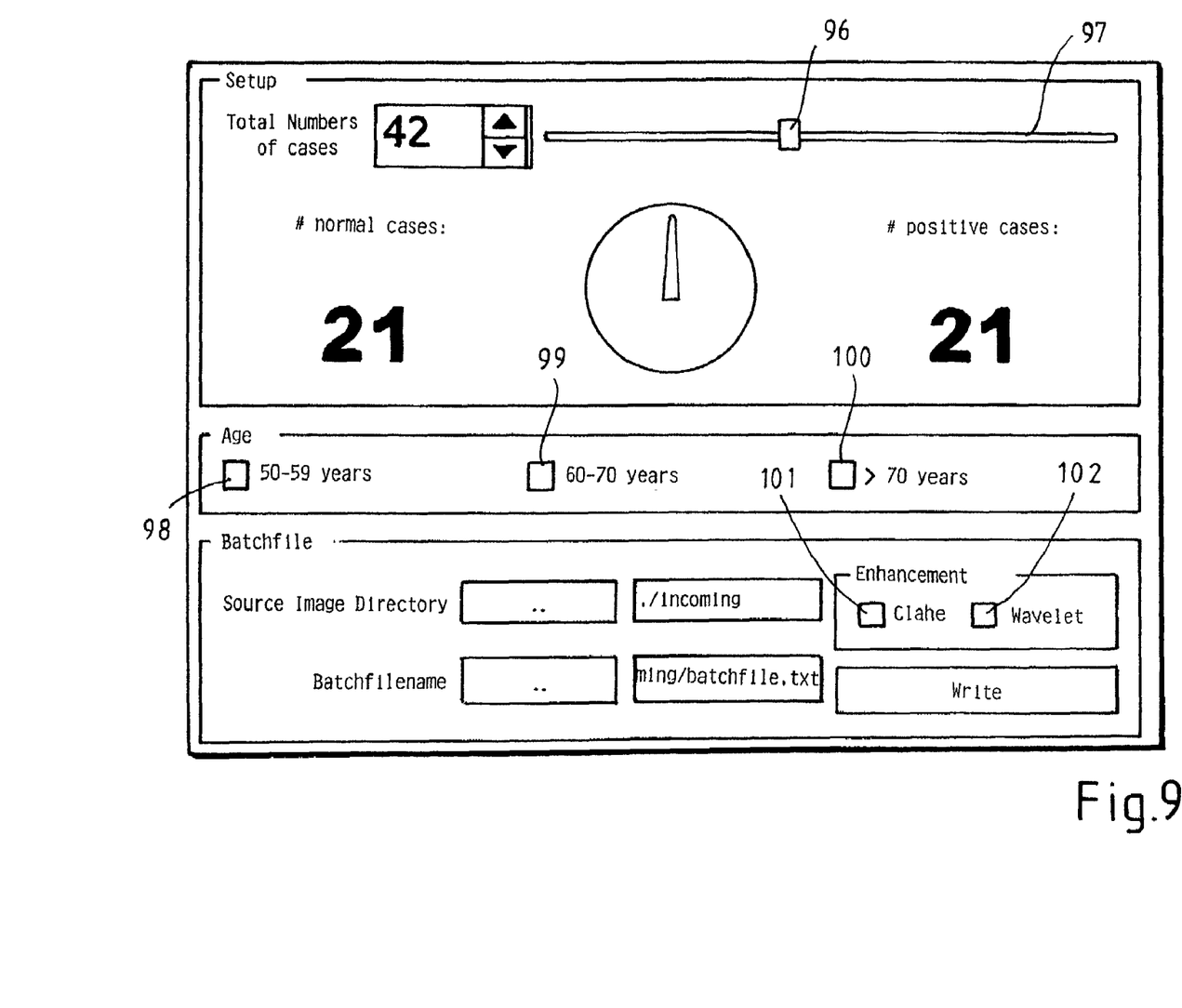
FIG. 9 is an input screen comprising a screening training sheet.

FIG. 9 shows an input screen for specifying a case profile to be reviewed for training purposes, such as screening training. The screen can also be used in order to specify known positive cases to be infiltrated for the purposes of the in-service monitoring.

The screen allows inputting the total number of cases—in this case 42 cases. A slide 96 can be moved along a line 97. The position of the slide 96 determines the distribution of normal and positive cases. As the slide 96 is in a middle position the same number of normal and positive cases is selected. Moving the slide 96 to the left proportionally increases the number of normal cases and decreases the number of positive cases such that the total number of cases remains the same. Moving the slide 96 to the right will correspondingly increase the number of positive cases and decreases the number of normal cases.

Clicking on one of the fields 98, 99 or 100 specifies the age distribution of patients from which the mammograms are taken—in this case 50 to 59, years, 60 to 70 years and greater 70 years.

Figure 10:
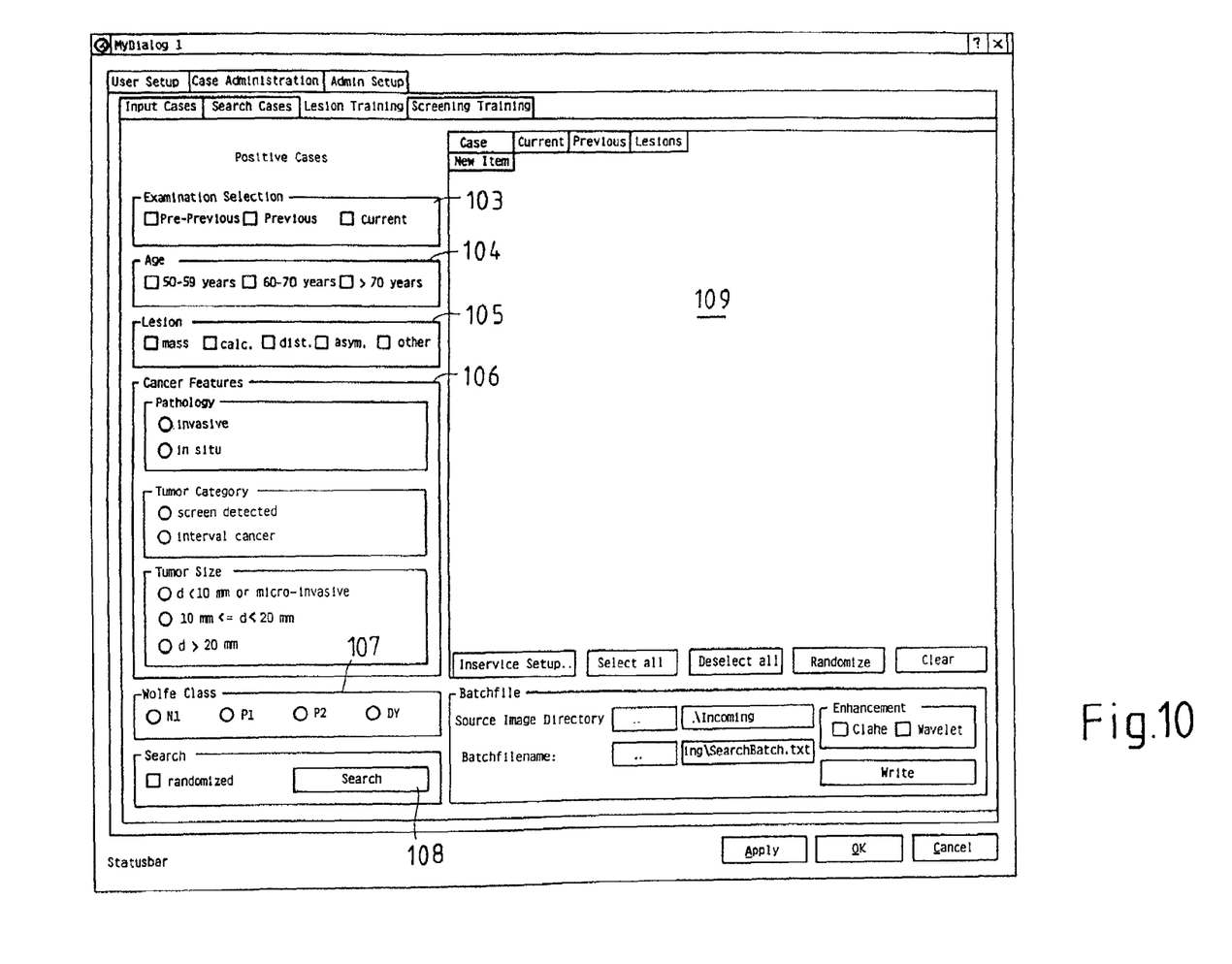
FIG. 10 is an input screen comprising a lesion training sheet.

FIG. 10 is a corresponding input screen for inputting of individual settings (cf. step 82). In the case of the lesion training only positive cases (either benign or malign) are to be reviewed by definition. The screen shown in FIG. 10 contains an entry field 103 for specifying if the current, a previous or a pre-previous mammogram is to be selected.

In the entry field 104 the age distribution can be specified. The entry field 105 serves to specify the type of lesion (mass, microcalcifications, architectural distortion (DIST.) asymmetric and other).

The entry field 106 serves to specify cancer features, such as pathology, tumor category and tumor size. The field 107 serves to input the Wolfe class. By clicking on the search button 108 a number of cases is selected from a case database corresponding to the search profile entered by means of the fields 103 to 107. The search result is displayed in the window 109.

Figure 11:
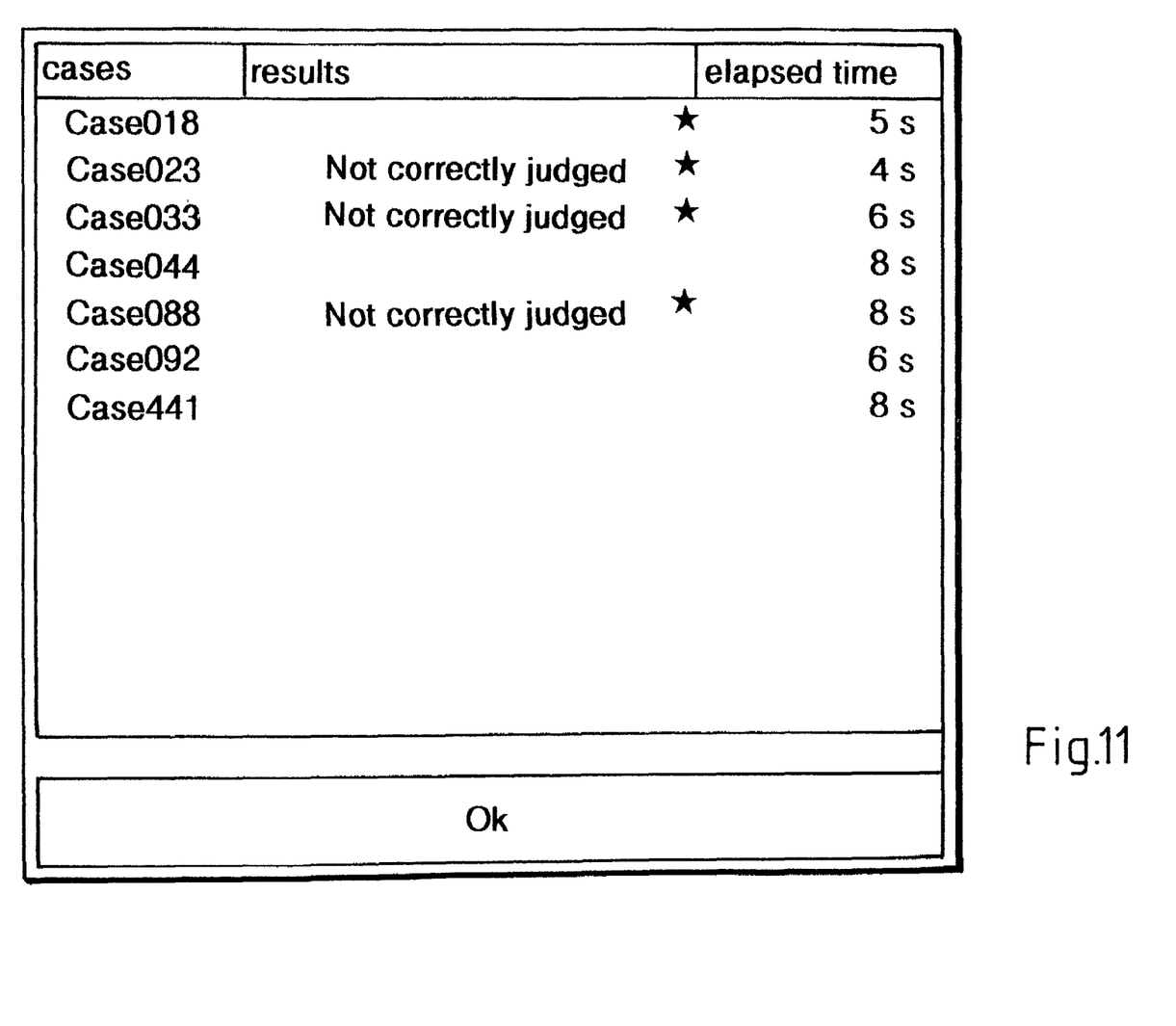
FIG. 11 is a screen for displaying the training results.

FIG. 11 shows the result of an overall evaluation. The left column of the screen shows the sequence of cases reviewed and the corresponding case IDs. The next column shows the corresponding result of the diagnosis. If an incorrect diagnosis has been entered the result is "not correctly judged". The right column shows the time required for the diagnosis of a particular case.

Although the present invention has been shown and described with respect to preferred embodiments, nevertheless, changes and modifications will be evident to those skilled in the art from the teachings of the invention. Such changes and modifications that embody the spirit, scope and teachings of the invention are deemed to fall within the purview of the invention as set forth in the appended claims.

LIST OF REFERENCE NUMERALS

| | |
|---|---|
| computer | 01 |
| user interface | 02 |
| user profile | 03 |
| keypad | 04 |
| next-step button | 05 |
| workflow memory | 06 |
| case stack | 07 |
| printer | 08 |
| image selection module | 09 |
| program | 10 |
| generator | 11 |
| retrieval program module | 12 |
| database | 13 |
| table | 14 |
| infiltration program module | 15 |
| database | 16 |
| table | 17 |
| session preparation module | 18 |
| display system | 19 |
| monitor | 20 |
| diagnosis database | 21 |
| database module | 22 |
| user action database | 23 |
| rules | 24 |
| input field | 25 |
| input field | 26 |
| input field | 27 |
| input field | 28 |
| slide | 96 |
| line | 97 |
| field | 98 |
| field | 99 |
| field | 100 |
| field | 101 |
| field | 102 |
| entry field | 103 |
| entry field | 104 |
| entry field | 105 |
| entry field | 106 |
| field | 107 |
| search button | 108 |
| window | 109 |

What is claimed is:

1. A computer system for in-service monitoring of a user screening medical cases comprising:
   a case stack of undiagnosed real cases to be reviewed by the user;
   a library of known cases;
   a user interface component for requesting a consecutive case, for display of the consecutive case, and for entering a diagnosis of the consecutive case;
   a program component for receiving a request for the consecutive case from the user interface, the program component selecting the consecutive case from the case stack of real cases and the library of known cases for the display and the diagnosis; and
   feedback component for outputting a message to the user if the user diagnosis of the selected known case is incorrect.

2. A computer system as set forth in claim 1 further comprising a pseudo-random component for generation of a pseudo-random number, the program component being coupled to the pseudo-random component for determining the selection of the consecutive case from the case stack of real cases or the library of known cases based on the output of the pseudo-random component.

3. A computer system as set forth in claim 1 further comprising a session preparation component for initializing the case stack and for specifying an absolute number or a percentage of known cases to be selected by the program component during the screening of the case stack by the user.

4. A computer system as set forth in claim 3 wherein the session preparation component enables specifying a category for the known cases.

5. A computer system as set forth in claim 1 further comprising a user action component for tracing of user input actions and of the feedback component.

6. A computer system as set forth in claim 5 further comprising a user action report generation component being coupled to the user action component for generating a user action report for the purposes of quality monitoring and assurance.

7. A computer system as set forth in claim 1 further comprising a mode selection component for selecting a random mode or a fixed mode for the operation of the program component.

8. A computer system for in-service monitoring of a user screening medical cases, comprising:
 a case stack of undiagnosed real cases to be reviewed by the user;
 a library of known cases having verified diagnoses;
 a user interface component for requesting a consecutive case, for displaying the consecutive case, and for entering a diagnosis of the consecutive case;
 a program component for receiving a request for the consecutive case from the user interface to be displayed and diagnosed, the program component selecting the consecutive case from the case stack of real cases and the library of known cases; and
 a feedback component for outputting a message to the user when a threshold of the known cases have been misdiagnosed per a given number of the real cases preceding the misdiagnosis.

9. The computer system according to claim 8, wherein said threshold is one.

10. The computer system according to claim 8, wherein said given number is a total number of the real cases.

11. The computer system according to claim 8, further comprising a timer, said timer preventing the user from making further diagnoses for a given amount of time after the threshold has been reached.

* * * * *